(12) United States Patent
Kislev et al.

(10) Patent No.: US 7,433,133 B2
(45) Date of Patent: Oct. 7, 2008

(54) OPTICAL SYSTEM

(75) Inventors: Hanoch Kislev, Zichron Yaakov (IL);
Arkady Glukhovsky, Nesher (IL);
Gavriel Meron, Petach Tikva (IL);
Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 11/115,320

(22) Filed: Apr. 27, 2005

(65) Prior Publication Data

US 2005/0185299 A1    Aug. 25, 2005

Related U.S. Application Data

(63) Continuation of application No. 10/879,276, filed on Jun. 30, 2004, now Pat. No. 6,934,093, which is a continuation of application No. 10/009,837, filed as application No. PCT/IL00/00349 on Jun. 15, 2000, now Pat. No. 6,836,377.

(30) Foreign Application Priority Data

Jun. 15, 1999    (IL)    ................................ 130486

(51) Int. Cl.
*G02B 13/18*    (2006.01)
*H04N 7/18*    (2006.01)
*A61B 1/06*    (2006.01)

(52) U.S. Cl. ................ 359/708; 359/728; 348/65; 600/160

(58) Field of Classification Search ............ 359/708
See application file for complete search history.

(56) References Cited

U.S. PATENT DOCUMENTS

| 3,745,325 A | 7/1973 | Harvey ................ 362/6 |
| 3,971,362 A | 7/1976 | Pope et al. ............ 600/302 |
| 4,005,287 A | 1/1977 | Cook ................ 250/239 |
| 4,017,163 A | 4/1977 | Glass ................ 359/365 |
| 4,234,912 A | 11/1980 | Barnes et al. ........ 362/145 |
| 4,278,077 A * | 7/1981 | Mizumoto ............ 600/109 |
| 4,596,050 A | 6/1986 | Rogers ................ 348/164 |
| 4,689,621 A | 8/1987 | Kleinberg ............ 340/870.17 |
| 4,819,620 A | 4/1989 | Okutsu ................ 600/114 |
| 4,844,076 A | 7/1989 | Lesho et al. ............ 600/302 |
| 4,936,823 A | 6/1990 | Colvin et al. | |
| 5,010,412 A | 4/1991 | Garriss | |

(Continued)

FOREIGN PATENT DOCUMENTS

DE    323 006    7/1920

(Continued)

OTHER PUBLICATIONS

The Radio Pill. Rowlands, et al, British Communications and Electronics Aug. 1960 pp. 598-601.

(Continued)

*Primary Examiner*—Jessica Stultz
(74) *Attorney, Agent, or Firm*—Pearl Cohen Zedek Latzer LLP

(57) ABSTRACT

The present invention provides an optical system for illuminating and viewing a target in which an illumination element and a receiving means are disposed behind a single optical window, and which obtains data essentially free of backscatter and stray light. The optical window of the optical system is configured such that it defines a shape having at least one focal curve, i.e., an ellipsoid shaped dome. The illumination element and the receiving means are geometrically positioned on the focal curve plane or in proximity of the focal curve plane, such that, when illuminating, rays from the illumination elements, that are internally reflected from the optical window, will not be incident on the receiving means.

9 Claims, 3 Drawing Sheets

U.S. PATENT DOCUMENTS

| | | | |
|---|---|---|---|
| 5,279,607 A | 1/1994 | Schentag et al. | 604/890.1 |
| 5,604,531 A * | 2/1997 | Iddan et al. | 348/76 |
| 5,681,260 A * | 10/1997 | Ueda et al. | 600/114 |
| 5,697,384 A | 12/1997 | Miyawaki et al. | |
| 5,718,663 A | 2/1998 | Wulfsberg | |
| 5,764,274 A | 6/1998 | Sousa et al. | 347/248 |
| 5,819,736 A | 10/1998 | Avny et al. | 600/407 |
| 5,840,014 A | 11/1998 | Miyano et al. | 600/125 |
| 5,993,378 A | 11/1999 | Lemelson | |
| 6,240,312 B1 * | 5/2001 | Alfano et al. | 600/476 |
| 6,416,181 B1 | 7/2002 | Kessler et al. | 353/7 |
| 6,428,469 B1 * | 8/2002 | Iddan et al. | 600/109 |
| 6,511,182 B1 | 1/2003 | Agostinelli et al. | 353/7 |
| 6,612,701 B2 | 9/2003 | Westort et al. | 353/10 |
| 6,709,387 B1 * | 3/2004 | Glukhovsky et al. | 600/109 |
| 6,764,440 B2 * | 7/2004 | Iddan et al. | 600/109 |
| 6,836,377 B1 | 12/2004 | Kislev et al. | |
| 6,934,093 B2 * | 8/2005 | Kislev et al. | 359/708 |
| 7,009,634 B2 | 3/2006 | Iddan et al. | |
| 2002/0103417 A1 | 8/2002 | Gazdzinski | |
| 2002/0198439 A1 * | 12/2002 | Mizuno | 600/109 |
| 2003/0020810 A1 * | 1/2003 | Takizawa et al. | 348/68 |
| 2003/0167000 A1 | 9/2003 | Mullick et al. | |
| 2003/0171648 A1 * | 9/2003 | Yokoi et al. | 600/109 |
| 2003/0171649 A1 * | 9/2003 | Yokoi et al. | 600/109 |
| 2003/0171652 A1 | 9/2003 | Yokoi et al. | |
| 2003/0208107 A1 | 11/2003 | Refael | |
| 2004/0073087 A1 * | 4/2004 | Glukhovsky et al. | 600/109 |
| 2004/0171914 A1 * | 9/2004 | Avni | 600/160 |
| 2005/0068416 A1 | 3/2005 | Glukhovsky et al. | |
| 2005/0185299 A1 | 8/2005 | Kislev et al. | |

FOREIGN PATENT DOCUMENTS

| | | |
|---|---|---|
| DE | 34 40 177 | 5/1986 |
| DE | 3928515 | 6/1990 |
| DE | 9016829 | 2/1991 |
| EP | 0667115 | 8/1995 |
| EP | 0 941 691 | 9/1999 |
| JP | 5745833 | 3/1982 |
| JP | 63-200115 | 8/1988 |
| JP | 03-264037 | 11/1991 |
| JP | 3264037 | 11/1991 |
| JP | 04-109927 | 4/1992 |
| JP | 4109927 | 4/1992 |
| JP | 1992-144533 | 5/1992 |
| JP | 5015515 | 1/1993 |
| JP | 08-248326 | 9/1996 |
| JP | 11-142933 | 5/1999 |
| JP | 2005-003828 | 6/2005 |
| WO | WO98/11816 | 3/1998 |
| WO | WO 00/22975 | 4/2000 |
| WO | WO 00/76391 A1 | 12/2000 |
| WO | WO 01/08548 | 2/2001 |
| WO | WO 01/65995 | 9/2001 |
| WO | WO 02/055126 | 7/2002 |
| WO | WO 02/095351 | 11/2002 |
| WO | WO 2004/035106 | 4/2004 |

OTHER PUBLICATIONS

Wellesley company sends body montiors into space—Crum Apr. 1998.

Wireless transmission of a color television moving image from the stomach using a miniature CCD camera, light source and microwave transmitter . Swain CP Gong F Mills TN Gastrointest Endosc 1997;45:AB40.

Manual of Photogrammetry, Thompson (Ed ), Third Edition, vol. Two, American Society of Photogrammetry. 1966.

BBC News Online—"Pill camera to 'broadcast from the gut'" Feb. 21, 2000 www news bbc co uk.

Katgraber F Glenewinkel F. Fischler S. Int J Legal Med 1998; 111(3) 154-6.

European Search Report of European Application 009371576, dated Feb. 3, 2004.

U.S. Appl. No. 11/291,906, filed Dec. 2, 2005, Kislev et al.

U.S. Appl. No. 11/221,841, filed Sep. 9, 2005, Glukhovsky.

US Office Action for U.S. Appl. No. 10/009,837 dated Oct. 2, 2003.

US Office Action for U.S. Appl. No. 10/009,837 dated Apr. 30, 2004.

US Office Action for U.S. Appl. No. 10/879,276 dated Dec. 14, 2004.

European Search Report. Application No. EP 06022666. Date of completion of the search Dec. 4, 2006.

European Search Report Dated Jan. 18, 2006 Application 05026710.3.

European Office Action Dated Nov. 16, 2006 Application 05026710.3.

Japanese Office Action Dated Aug. 2, 2005 Application 2001-502738.

Japanese Office Action Dated Aug. 2, 2005 Application 2005-155953.

* cited by examiner

OPTICAL SYSTEM

CROSS REFERENCE TO RELATED APPLICATIONS

This application is a continuation of U.S. patent Ser. No. 10/879,276 filed Jun. 30, 2004, entitled, "AN OPTICAL SYSTEM", now U.S. Pat. No. 6,934,093, which is a continuation of U.S. patent application Ser. No. 10/009,837, filed Aug. 22, 2002, entitled, "AN OPTICAL SYSTEM", now U.S. Pat. No. 6,836,377, which is a national phase application of PCT Application no. PCT/IL00/00349, filed 15 Jun. 2000, which claims benefit from Israeli Patent Application no. IL 130486, filed 15 Jun. 1999, all of which being incorporated in their entirety herein by reference.

FIELD OF THE INVENTION

The present invention relates to an optical system for illuminating and viewing a target.

BACKGROUND OF THE INVENTION

An optical system for illuminating and viewing a target, which comprises a target, a source of illumination of the target and means for receiving the light remitted from the target, can be defined by an illumination axis and optical axis that converge at the target.

Such an optical system may be as simple as an operator of an illumination source viewing a target, wherein the operator embodies the means for receiving the light remitted from the target. An example of such an optical system is an operator of a vehicle, that is inside the vehicle and is looking out at an illuminated target such as a road or tunnel walls.

More complex optical systems include automated processors as means for receiving the light remitted from a viewed target. Examples of such optical systems can be found in diagnostic apparatuses such as endoscope devices. The endoscopes described in the art comprise an image pickup element and an illuminating element for illuminating an examined target.

For these optical systems it is advantageous to have the illuminating element and receiving means contained within a single compartment, namely behind a single optical window.

In a vehicle carrying an operator, the illuminating elements are usually situated outside the vehicle, thereby requiring the operator to leave the vehicle for repairs or the like. In vehicles such as submarines or trains travelling in a dark tunnel, this may be a perilous task.

In diagnostic apparatuses, especially those meant to be inserted into body orifices, having a single optical window is advisable for hygienic and practical considerations.

A frequent problem encountered in having the illumination element and means for receiving remitted light contained behind a single optical window is the "noise" (backscatter and stray light) produced by light remitted from the optical window itself, which is received by the receiving means.

Presently used techniques for reducing noise include utilizing light guiding means, or separating the illumination element from the receiving means.

For example, U.S. Pat. No. 5,840,014 (Miyano et al.) describes an endoscope having an illumination window and a viewing window having a detachable protective covering and a transparent material for purging air from the space between the front end and the detachable covering, for lowering loss in illumination light quantity.

SUMMARY OF THE INVENTION

The present invention provides an optical system for illuminating and viewing a target in which an illumination element and a receiving means are disposed behind a single optical window, and which obtains data essentially free of backscatter and stray light.

The optical system according to the present invention comprises at least one illumination element and at least one receiving means, both disposed behind a single optical window having a plurality of reflecting surfaces.

The optical window is configured such that it defines a shape having at least one focal curve.

At least one illumination element and at least one receiving means are geometrically positioned on the focal curve plane or in proximity of the focal curve plane, such that, when illuminating, rays from the illumination elements, that are internally reflected from the optical window surfaces, will not be incident on the receiving means.

It will be appreciated that the term "receiving means" relates to any means suitable for receiving, processing or further transmitting illumination rays remitted from a target or data derived from these rays.

In an embodiment of the invention the optical window is an ellipsoid shaped dome. A plurality of illumination elements are positioned on the ellipsoid focal curve and a receiving means is positioned on the axis of symmetry of the ellipsoid at an equal distance from the illumination elements.

The components of the system, thus positioned, ensure that when illuminating, all the light internally reflected from the optical window surfaces is received at points on the focal curve and is not incident on the receiving means.

The present invention further provides a diagnostic instrument comprising an optical system according to the present invention.

BRIEF DESCRIPTION OF THE DRAWINGS

The present invention will be understood and appreciated more fully from the following detailed description taken in conjunction with the figures in which.

DETAILED DESCRIPTION OF THE INVENTION

The present invention relates to an optical system based on geometrically positioning both illumination elements and means for receiving light behind a single optical window, such that internally reflected light from the optical window will not be incident on the receiving means.

The optical window, which is made of any suitable glass or plastic, can be viewed as being assembled from infinitesimal level surfaces, each level surface internally reflecting an illumination ray incident on it at a reflection angle equal to the angle of incidence. The level surfaces are angled to each other such that reflected illumination rays are always converged at a single known point.

This assembly can result in a shape having focal points (for example, an ellipse) and an optical window thus assembled would have the optical property that light rays emitted from one focal point, which are internally reflected, will be propagated to the second focal point. In a three dimensional shape (such as an ellipsoid) light rays emitted from a point on a focal curve, which are internally reflected, will be propagated to another point on the focal curve.

For example, in the field of arc lamp systems this property is used to collect energy efficiently. For example in Model A-1010 and A-1010B lamp housings provided by Photon Technology International of New Jersey, USA, an arc source is located at a foci of an ellipsoid reflector and the radiation is reflected to another foci. Energy is collected efficiently since the light is brought to a focus by reflection rather than by refraction (through a lens) such that there is no loss due to absorption or lens surface back reflection.

In the optical system of the present invention the illumination elements are positioned on focal points and the receiving means' position does not coincide with the focal points, thus ensuring that internally reflected light is propagated to focal points and not received by the receiving means.

Figure 1A:
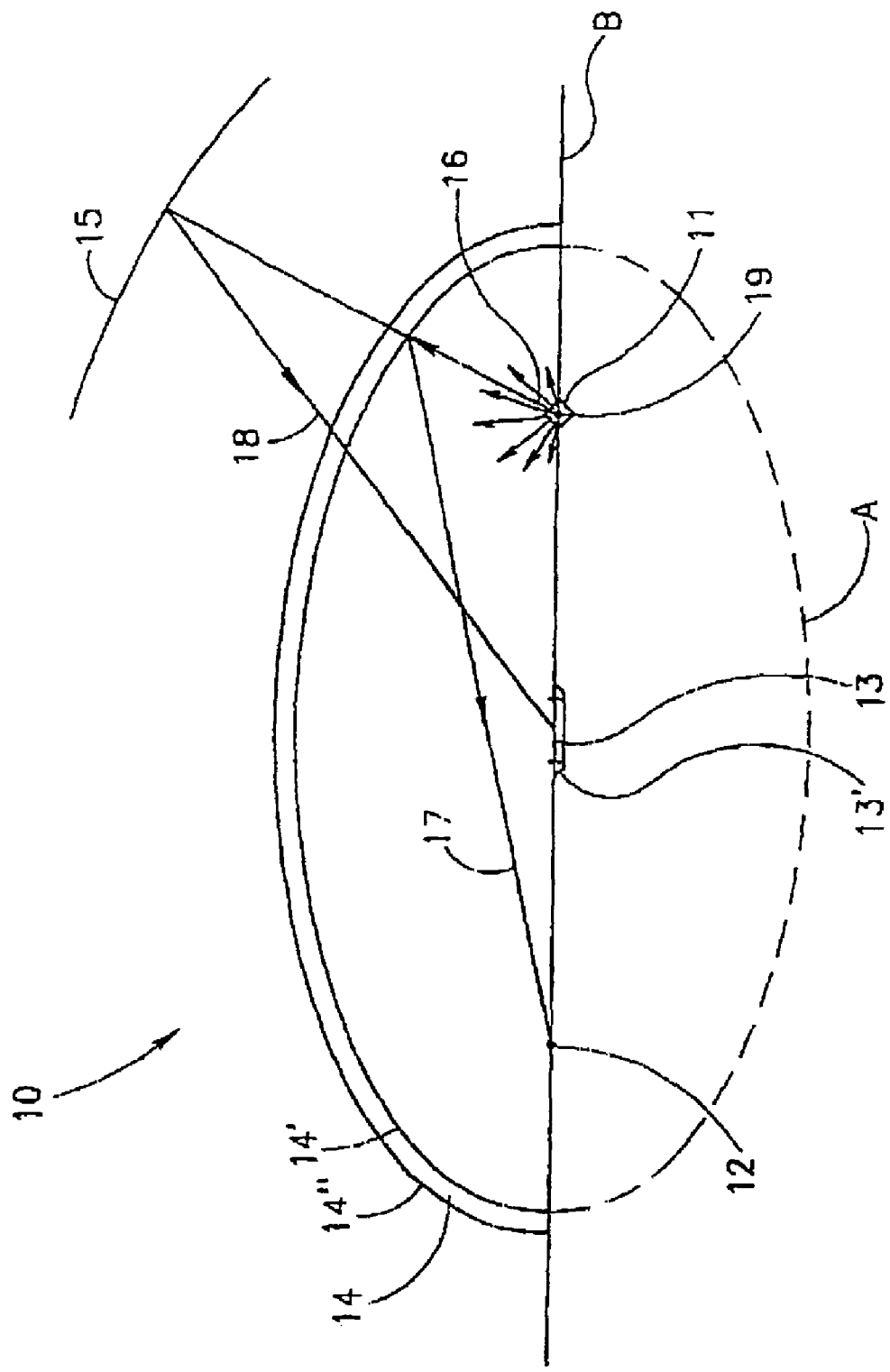
FIGS. 1A and 1B are schematic two and three dimensional illustrations, respectively, of an optical system according to the present invention.

Reference is now made to FIG. 1A which is a schematic two dimensional presentation of an optical system according to the present invention.

FIG. 1A is a two dimensional illustration of an optical system generally referenced 10. The optical system 10 comprises an illumination element 11 and receiving means 13, both disposed behind an optical window 14, for viewing target 15. Optical window 14 has a surface configured such that a shape defined by it and by broken line A has an axis of symmetry B and two focal points 19 and 12. Illumination element 11 is positioned on focal point 19 and receiving means 13 is positioned on the axis of symmetry B not coinciding with either focal point 19 or 12.

The course of light rays emitted from illumination element 11 will be followed as an example of the behavior of illumination rays in the optical system of the invention. Light 16 is emitted from illumination element 11 (which element's position coincides with focal point 19) for illuminating target 15. A certain percent of the light (represented by ray 17) is internally reflected from the optical window 14 surfaces 14' and 14" and is propagated to the second focal point 12. A percent of the light 16 (represented by ray 18) is incident on target 15, is reflected from target 15 and received by receiving means 13.

Thus, internally reflected light rays (such as ray 17) are propagated to areas outside the receiving means 13 area.

Receiving means 13 is also unexposed to direct illumination from illumination element 11. Illumination element 11 may illuminate light 16 in a circular band that is tangent to line B. In this case, if receiving means 13 is positioned on line B it will not receive any direct illumination rays from illumination element 11. Alternatively, receiving element 13 can be concealed in a niche 13' to avoid receiving direct illumination rays from illumination element 11.

Thus, geometric positioning of the components of the system ensures that no backscatter, such as ray 17, and no direct light, only incident light, such as ray 18, is received by receiving means 13.

In actuality, the optical window 14 is a three dimensional shape. A three dimensional representation of the optical system 10 of FIG. 1A, is shown in FIG. 1B.

Figure 1B:
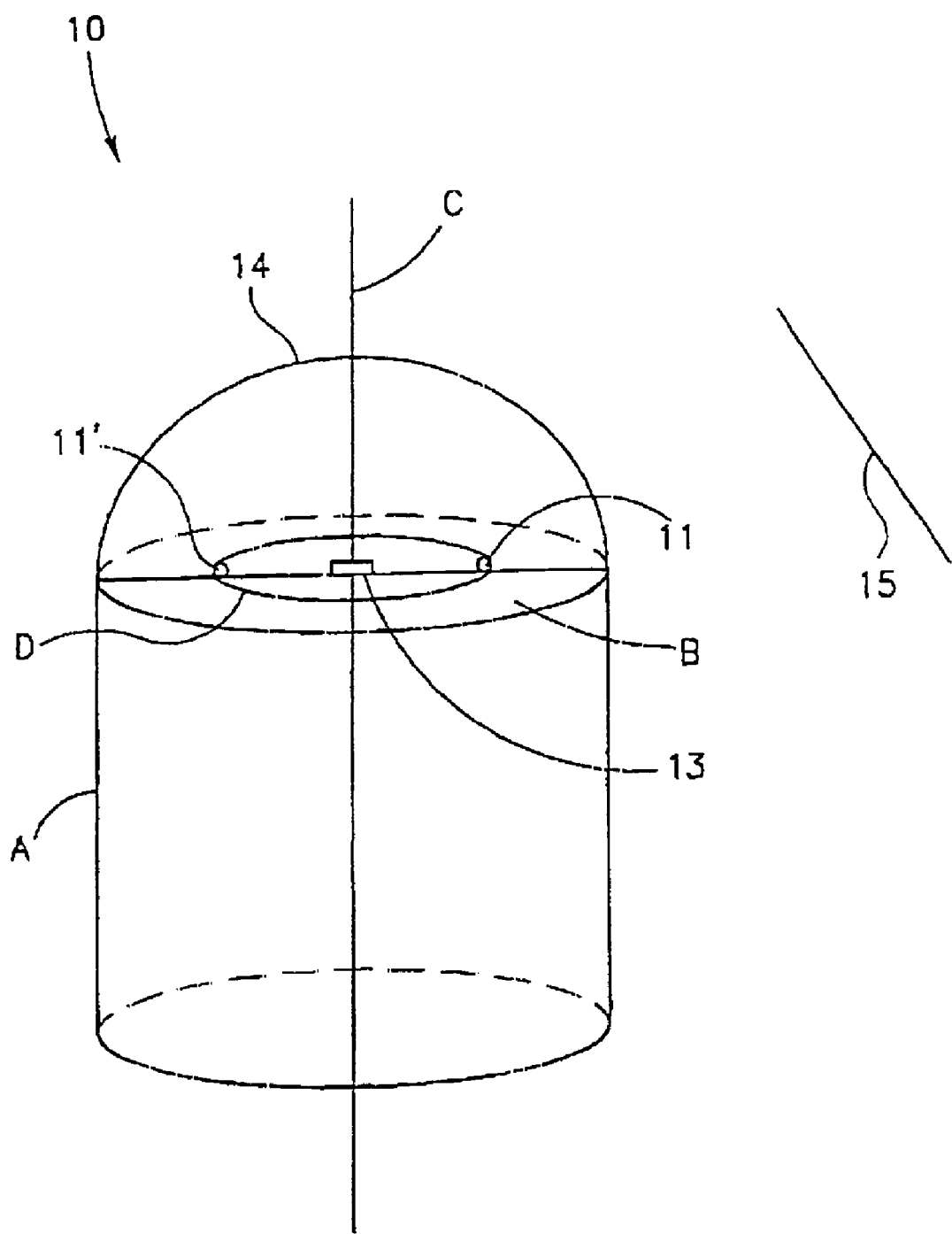

In the optical system 10 shown in FIG. 1B plane B, formed along line B from FIG. 1A, is shown. Axis C is perpendicular to plane B. The shape on plane B which is defined by optical window 14, encompasses focal curve D.

A plurality of illumination elements, such as 11 and 11', may be positioned on focal curve D to enable a uniform spatial illumination, though it should be appreciated that any number of illuminating elements can be used according to specific requirements of the system.

Receiving means 13 is positioned at a point which is on, or in the vicinity of, axis C, essentially at an equal distance from both illuminating elements 11 and 11', and on, or in the vicinity of plane B, such that it receives incident light remitted from target 15. All the light radiated from illuminating elements 11 and 11' that is internally reflected from the optical window surfaces is received at points on focal curve D and is not incident on receiving means 13.

Thus data obtained by receiving means 13 is essentially free of backscatter and stray light.

Figure 2A:
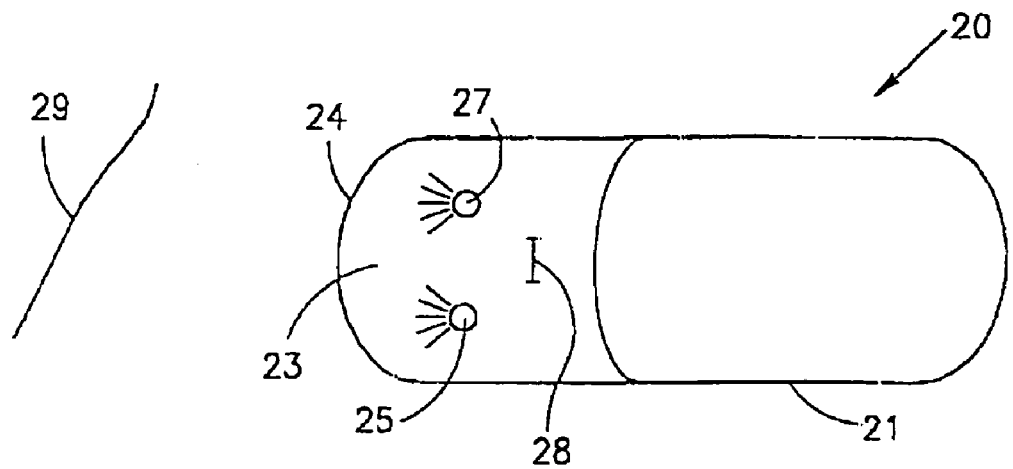
FIGS. 2A and 2B are schematic illustrations of two embodiments comprising the optical system of the present invention; a diagnostic device and a vehicle carrying receiving means, respectively.
Figure 2B:
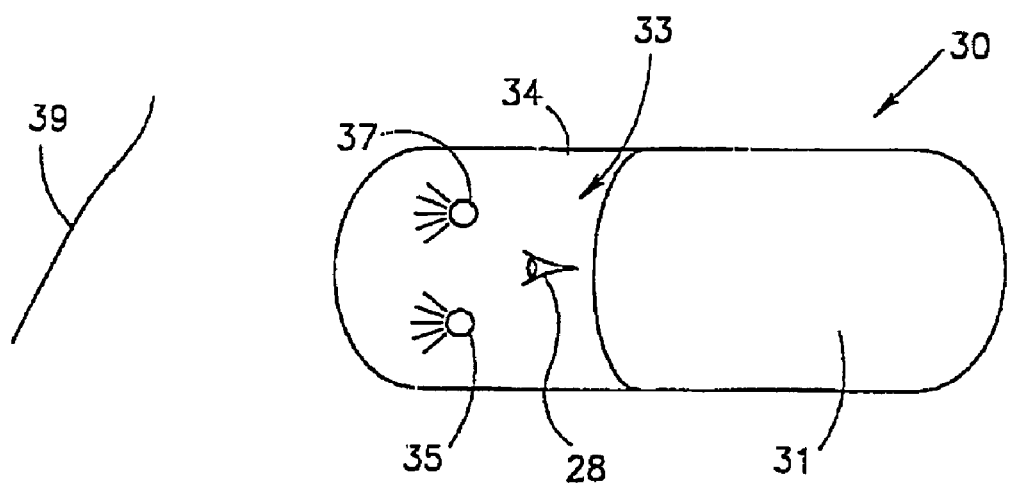

Two of the possible applications for the optical system of the present invention are provided as two different embodiments, illustrated in FIGS. 2A and 2B.

FIG. 2A illustrates a swallowable capsule which includes a) a camera system, b) an optical system for imaging an area of interest onto the camera system and c) a transmitter which transmits the video output of the camera system. Such a swallowable capsule is disclosed in U.S. Pat. No. 5,604,531, assigned to the common assignees of the present application, which is hereby incorporated by reference. The swallowable capsule can pass through the entire digestive tract and thus, operates as an autonomous video endoscope.

The capsule, generally referenced 20 is shaped as an ellipsoid. The capsule 20 comprises a housing unit 21 and a viewing unit 23, for viewing a target point 29 on the digestive tract wall. The viewing unit 23 comprises an optical system according to the invention.

The optical system comprises a protective optical window 24, preferably made of isoplast, two illumination elements 25 and 27 and an imaging device 28. Illumination elements 25 and 27 are positioned on a focal plane perpendicular to the axis of symmetry of the ellipsoid defined by the body of the capsule 20. The imaging device 28, such as a camera, is positioned on the axis of symmetry of the capsule 20.

Light rays emitted from illumination elements 25 and 27, that reach a target point 29 on the digestive tract wall are reflected to imaging device 28, whereas light rays internally reflected from protective optical window 24 are propagated to points on the focal curve and not to imaging device 28.

It will be appreciated that protective optical window 24, being a single and complete unit, is easily disposable, and can be smoothly replaced between different passes through the digestive tract. This fact, which is not affordable by endoscopes described in the art, contributes to the sterile and facile use of a diagnostic device comprising the optical system of the invention.

Thus, the present invention provides a simply assembled diagnostic device which can obtain data, essentially free of noise such as backscatter and stray light.

FIG. 2B illustrates a vehicle, such as a submarine, generally referenced 30. Submarine 30 is shaped such that its eccentricity is equal to or larger than zero and smaller than 1.

The submarine 30 comprises a propulsion unit 31 and a viewing cell 33, encased by window 34, in which an operator or a monitoring device 38 are positioned on the axis of symmetry of the shape of submarine 30. A target of interest 39, in the deep waters, is being viewed. The target of interest 39 is illuminated by illumination elements 35 and 37 that are positioned on a focal plane of the shape defined by the body of the submarine 30, such that light rays internally reflected from window 34 do not blind the operator and/or are not received by monitoring device 38.

The invention claimed is:

1. A swallowable capsule for imaging the digestive tract, the capsule comprising:
   a dome-shaped protective optical window comprising an outside surface and an inside surface, the inside surface being concave;
   a plurality of illumination elements;
   a receiving means for receiving light rays reflected from the digestive tract wall wherein the capsule images along a longitudinal axis of the capsule;
   wherein the receiving means and all of the illumination elements are positioned behind the dome-shaped protective optical window such that the digestive tract is illuminated through the dome-shaped optical window and wherein the receiving means is at an essentially equal distance from each of the illumination elements.

2. The capsule as in claim 1 wherein the receiving means comprises a camera system.

3. The capsule as in claim 1 comprising a transmitter for transmitting output of the camera system.

4. A swallowable capsule for imaging the digestive tract, the capsule comprising:
   a dome-shaped protective optical window defining a shape having an axis of symmetry, the axis of symmetry being located along a longitudinal axis of the capsule, the window comprising an outside surface and an inside surface, the inside surface being concave;
   a plurality of illumination elements;
   a receiving means for receiving light rays reflected from the digestive tract wall;
   wherein the receiving means is positioned on the axis of symmetry and wherein the receiving means and all of the Illumination elements are positioned behind the dome-shaped protective optical window such that the digestive tract is illuminated through the dome-shaped optical window and wherein the capsule images along the longitudinal axis of the capsule.

5. The capsule of claim 4 wherein the plurality of illumination elements are positioned on a plane perpendicular to the axis of symmetry.

6. A swallowable capsule for imaging the digestive tract, the capsule comprising:
   a dome-shaped protective optical window comprising an outside surface and an inside suite; the inside surface being concave,
   a plurality of illumination elements,
   a receiving means for receiving light rays reflected from the digestive tract wall;
   wherein all of the illumination elements are positioned behind a single optical window so as to enable uniform spatial illumination of the gastrointestinal tract wall, such that the digestive tract is illuminated through the dome-shaped optical window, and wherein the capsule images along a longitudinal axis of the capsule.

7. The capsule of claim 6, wherein the illumination elements are positioned on a plane.

8. The capsule of claim 7, wherein the plane is perpendicular to an axis of symmetry of the capsule.

9. The capsule of one of claims 6, wherein the protective optical window is made of plastic.

* * * * *

(12) EX PARTE REEXAMINATION CERTIFICATE (9880th)
United States Patent
Kislev et al.

(10) Number: US 7,433,133 C1
(45) Certificate Issued: Oct. 17, 2013

(54) OPTICAL SYSTEM

(75) Inventors: Hanoch Kislev, Zichron Yaakov (IL);
Arkady Glukhovsky, Nesher (IL);
Gavriel Meron, Petach Tikva (IL);
Gavriel J. Iddan, Haifa (IL)

(73) Assignee: Given Imaging Ltd., Yoqneam (IL)

Reexamination Request:
No. 90/012,565, Dec. 19, 2012

Reexamination Certificate for:
Patent No.: 7,433,133
Issued: Oct. 7, 2008
Appl. No.: 11/115,320
Filed: Apr. 27, 2005

Related U.S. Application Data

(63) Continuation of application No. 10/879,276, filed on Jun. 30, 2004, now Pat. No. 6,934,093, which is a continuation of application No. 10/009,837, filed as application No. PCT/IL00/00349 on Jun. 15, 2000, now Pat. No. 6,836,377.

(30) Foreign Application Priority Data

Jun. 15, 1999 (IL) .......................................... 130486

(51) Int. Cl.
*G02B 13/18* (2006.01)
*A61B 1/06* (2006.01)
*H04N 7/18* (2006.01)

(52) U.S. Cl.
USPC ........ 359/708; 359/728; 348/65; 348/E7.085; 600/160

(58) Field of Classification Search
None
See application file for complete search history.

(56) References Cited

To view the complete listing of prior art documents cited during the proceeding for Reexamination Control Number 90/012,565, please refer to the USPTO's public Patent Application Information Retrieval (PAIR) system under the Display References tab.

*Primary Examiner* — Christina Y Leung

(57) ABSTRACT

The present invention provides an optical system for illuminating and viewing a target in which an illumination element and a receiving means are disposed behind a single optical window, and which obtains data essentially free of backscatter and stray light. The optical window of the optical system is configured such that it defines a shape having at least one focal curve, i.e., an ellipsoid shaped dome. The illumination element and the receiving means are geometrically positioned on the focal curve plane or in proximity of the focal curve plane, such that, when illuminating, rays from the illumination elements, that are internally reflected from the optical window, will not be incident on the receiving means.

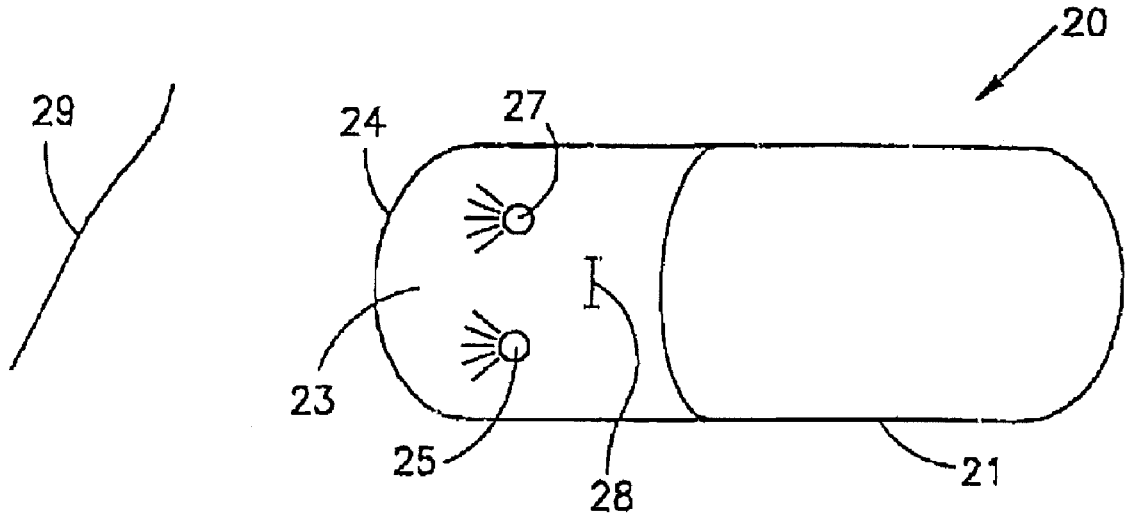

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-5 is confirmed.

Claim 6 is determined to be patentable as amended.

Claims 7-9, dependent on an amended claim, are determined to be patentable.

6. A swallowable capsule for imaging the digestive tract, the capsule comprising:
   a dome-shaped protective optical window comprising an outside surface and an inside [suite] *surface*; the inside surface being concave,
   a plurality of illumination elements,
   a receiving means for receiving light rays reflected from the digestive tract wall;
   wherein all of the illumination elements are positioned behind a single optical window so as to enable uniform spatial illumination of the gastrointestinal tract wall, such that the digestive tract is illuminated through the dome-shaped optical window, and wherein the capsule images along a longitudinal axis of the capsule.

* * * * *